United States Patent [19]
Kitajima et al.

[11] 4,248,829
[45] Feb. 3, 1981

[54] INTEGRATED ANALYTICAL MATERIAL SUITABLE FOR SIMULTANEOUSLY PERFORMING A PLURALITY OF ANALYSES

[75] Inventors: Masao Kitajima; Asaji Kondo; Fuminori Arai, all of Asaka, Japan

[73] Assignee: Fuji Photo Film Co., Ltd., Minami-ashigara, Japan

[21] Appl. No.: 101,385

[22] Filed: Dec. 7, 1979

[30] Foreign Application Priority Data

Dec. 11, 1978 [JP] Japan .......................... 53/170658[U]

[51] Int. Cl.³ ...................... G01N 33/52; G01N 31/22
[52] U.S. Cl. ........................................ 422/56; 422/57; 435/4; 435/805
[58] Field of Search ................. 422/56, 57; 23/230 B; 435/805

[56] References Cited

U.S. PATENT DOCUMENTS

| | | | |
|---|---|---|---|
| 3,791,933 | 2/1974 | Moyer | 435/805 X |
| 3,810,739 | 5/1974 | Nussbaum | 435/805 X |
| 4,050,898 | 9/1977 | Goffe | 422/57 |
| 4,061,468 | 12/1977 | Lange | 422/56 |
| 4,066,403 | 1/1978 | Bruschi | 23/230 B X |
| 4,144,306 | 3/1979 | Figueras | 422/56 |
| 4,160,008 | 7/1979 | Fenocketti | 422/56 |
| 4,166,093 | 8/1979 | Smith-Lewis | 422/56 |

*Primary Examiner*—Sidney Marantz
*Attorney, Agent, or Firm*—Sughrue, Rothwell, Mion, Zinn and Macpeak

[57] ABSTRACT

An integrated material for chemically analyzing a liquid sample comprising a supporting plate having provided thereon two or more different analytical units each comprising a reagent layer and a porous spreading layer or a portion of a common porous spreading layer, the units being disposed such that at least a portion of the reagent layers are in contact with or in close proximity to one another with the porous spreading layer(s) of the units being commonly covered with a liquid sample delivering patch.

1 Claim, 6 Drawing Figures

INTEGRATED ANALYTICAL MATERIAL SUITABLE FOR SIMULTANEOUSLY PERFORMING A PLURALITY OF ANALYSES

BACKGROUND OF THE INVENTION

1. Field of the Invention

This invention relates to integrated multilayer materials for chemical analyses of liquid samples comprising a supporting plate having disposed thereon a plurality of different analytical units each unit fundamentally comprising a reagent layer and a spreading layer, and a common liquid delivering patch is provided so as to ensure delivery of the liquid sample to the spreading layer of each analytical unit by only one application of sample.

2. Description of the Prior Art

Inventions relating to multilayer analytical materials fundamentally comprising a reagent layer and a spreading layer are described in, for example, U.S. Pat. Nos. 3,526,480, 3,663,374, 3,983,005, 3,992,158, 4,042,335, 4,050,898 and 4,066,403 and *Preparatory Papers for Publication at the 10th International Meeting of the Clinical Chemical Society* (held in Mexico City, Feb. 26–Mar. 3, in 1978), pages 13, 14, 47, 76 and 118, etc. Such multilayer analytical materials incorporate an analytical reagent in a binder such as gelatin. In practice, all that is required for chemical analysis is to apply or adhere one drop of a test sample to the material. Thus, they are dry type chemical analysis materials requiring no reagent solutions, test tubes, etc.

The fundamental construction of these multilayer materials comprises a porous spreading layer and a reagent layer. In some cases, the reagent layer is made up of a plurality of sublayers sharing different functions, for example, where two reagents (such as in a two-step reaction) are required for analysis, a second reagent layer may be located under a first reagent layer; or the analytical reaction products may be registered in a layer separate from the reagents such as in a color-forming layer, a detecting layer, or a dye-receiving layer. Also, interlayers or so-called radiation-blocking layers, barrier layers, etc., may be provided between the plurality of reagent layers. Further, there are structures wherein a reagent is incorporated in the spreading layer and thus the spreading function and the assay function may be integrated. In any event, the two functions of sample-spreading and reagent analysis are fundamental.

A liquid sample dropped or applied onto multi-layered chemical analysis material is uniformly spread through the porous spreading layer as it reaches the surface of the reagent layer. The ingredient contained in the sample solution (analyte) or a by-product thereof reacts with the reagent and produces coloration or discoloration enabling optical chemical analysis and in particular colorimetric analysis, whereby the presence and the content of the ingredient contained in the sample solution is detected.

The above-described multilayer analytical materials are quite convenient for chemically analyzing a single chemical ingredient contained in a liquid sample such as saliva, blood, urine, etc., rapidly and easily in a dry manner without using test tubes and reagent solutions. With these materials, however, an exclusive analytical material is necessary for every item analyzed, for example, a different material would be required for determining glucose, urine nitrogen, and amylase in blood. Thus for the analysis of six blood ingredients such as bilirubin, albumin, and cholesterol in addition to the above three ingredients, six different multilayered materials must be selected, 5 $\mu l$ to 15 $\mu l$ of whole blood or serum must be dropped or applied to each of the six materials and, after the completion of color reaction, colorimetry must be sequentially conducted.

Multilayer chemical analysis materials are quite excellent from the standpoint of the easiness of the determination. For example, in the chemical analysis of blood, they are quite convenient for analyzing one item per patient. However, generally clinical chemical examinations check 5 to 10 times per patient per blood drawing in which case the above procedure of selection, application, and examination can become quite burdensome and complicated.

SUMMARY OF THE INVENTION

As a result of various experiments to minimize the number of times application must be repeated when using multilayered analytical materials, the inventors found that an integrated plate comprising a supporting plate having integrated thereon a plurality of the different necessary multilayer analytical units in a particular disposition (e.g., a radial or stripe disposition) enables plural examinations of a liquid sample by dropping or applying sample onto only one point from which it is spread over each of the respective multilayer units (Japanese Patent Application No. 106850/78 (corresponding to U.S. patent application Ser. No. 71,618, filed Aug. 31, 1979, or to West German Patent Application No. P 29 34 760.2, filed Aug. 28, 1979)).

The present invention is an improvement in the aforementioned materials wherein a patch for delivering a liquid sample is provided on an integrated material suitable for a plurality of analyses at one time. The liquid sample delivering patch ensures that liquid sample uniformly reaches the different analytical units integrated on the plate through one application of the sample solution.

Throughout this disclosure, the term "integrated plate" or "integrated material" refers to an analytical material suitable for performing a plurality of analyses at one time and the term "analytical unit" refers to the individual units which are the basis for the plurality of analyses and which are integrated on a plate in accordance with the present invention.

This invention is an integrated analytical material comprising a supporting plate having provided thereon two or more different analytical units, each unit comprising a reagent layer and a porous spreading layer, positioned such that at least the reagent layers of these units are in contact with or in close proximity to one another and the porous spreading layers of the individual units being commonly covered by a liquid sample delivering patch.

BRIEF DESCRIPTION OF THE DRAWINGS

FIG. 5 is a top view and FIG. 6 is a cross-sectional view along the line $X_5$—$Y_5$ of FIG. 5.

DETAILED DESCRIPTION OF THE INVENTION

Figure 1:
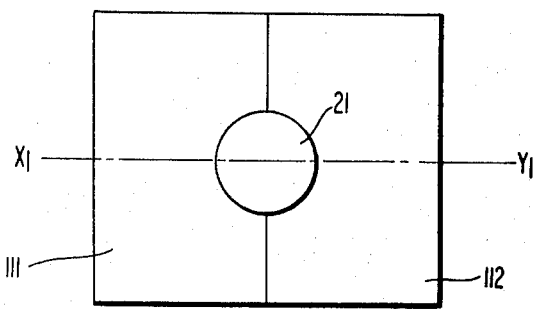
FIGS. 1 and 2 are overhead and cross-sectional views showing the fundamental structure of integrated plate of the present invention.

In this invention the reagent layers are disposed in contact with or in close proximity to one another. This means that the reagent layers and any other layers making up the individual analytical units are disposed such that at least one end or side thereof is within the area in which a liquid sample applied to the porous spreading layer spreads. Where the porous spreading layer has a continuous and substantially uniform structure, a line at the front edge of the area to which a liquid sample applied to a centrally located point above the spreading layer (center point) spreads through the spreading layer, forms a closed circle or approximately circular figure with the center point being approximately the center thereof. (Hereafter the area in which the sample is spread is referred to as the "spreading circle"). More particularly, this means that sufficient areas of the individual reagent layers of the analytical units (hereinafter referred to as the "chemical analysis region") are positioned within the spreading circle to analyze the sample by optical means.

In chemical analysis using the integrated plate of the present invention, the amount of a liquid sample applied is often limited mainly to facilitate procedures and shorten the time required for a series of the procedures (from the application of the liquid sample to the completion of chemical analysis) as much as possible. For the above-described practical reason, the radius of the spreading circle is about 3 mm to about 30 mm, preferably about 3 mm to about 20 mm. On the other hand, the analysis regions must exist within the spreading circle. Therefore, analytical units are disposed so that their analysis regions exist within a radius of not more than about 30 mm, preferably not more than about 20 mm, from the center point.

As specific examples of the arrangement of two or more different analytical units, there are illustrated radial arrangements wherein one apex of each of fan shapes, polygons such as triangles, rhombuses, rectangles, squares, etc., are in contact with each other at the center point or within a circle of a given radius around the center point; arrangements wherein polygons, circles, ellipses, or ovoid forms are inside a circle of a given radius around the center point; lattice pattern arrangements within a given radius around the center point; parallel arrangements within a given radius around the center point; and irregular arrangements (for example, a combination of arrangements) within a given radius from the center point. The radius described herein is equal to, or less than, that of the spreading circle. Preferably a liquid sample is spread through the porous spreading layer uniformly (i.e., in an equal amount per unit area), reaches the reagent layer at equal distances from the center point, and hence the two former arrangements are preferred.

The number of the analytical units disposed in the integrated plate of the present invention is two or more, preferably three or more. Obviously the greater the number the higher are the possible efficiencies.

Plates or laminates as the supporting plates can be used having a thickness of about 10 $\mu$m to about 0.5 mm, preferably about 20 $\mu$m to about 0.3 mm which are made of materials having a good transparency to near ultraviolet rays, visible light, and near infrared rays, such as polyesters (e.g., polyethylene terephthalate, bisphenol polycarbonate, etc.), cellulose esters (e.g., cellulose diacetate, cellulose triacetate, cellulose acetate propionate, cellulose acetate butyrate, cellulose nitrate, etc.), polystyrene, optical glass, etc. The supporting plate may be framed partly or wholly along the periphery thereof. The use of the aforesaid materials or other supporting plates (e.g., semi-transparent or opaque materials such as paper, plastics, metal foils, etc.) thinly coated with a matting agent like silicone resin adds protection and is delaminated prior to examination. In the case of using such delaminatable supporting plate, it is preferable to provide one porous spreading layer common to the respective analytical units to add support to the structure of the integrated plate.

The spreading layer is a layer that can accept a liquid sample and distribute it such that a uniform apparent concentration of the sample is provided at the surface of the spreading layer facing the reagent layers of the analytical units. The extent of spreading is dependent in part on the volume of the sample, however, a uniform apparent concentration is obtained per unit area at the surface facing the reagent layer upon spreading. Useful spreading layers may be prepared from a variety of materials as is described in U.S. Pat. No. 4,043,335. For example, a particulate material such as titanium dioxide, barium sulfate, diatomaceous earth, microcrystalline colloidal materials, etc., may be used to form such layers. Alternatively, or in addition, the spreading layer can be prepared using isotropically porous polymer compositions.

Spreading layers can be prepared by coating from a solution or dispersion. The thickness of the spreading layer varies and depends in part on the intended sample volume. Spreading layers of from about 50 $\mu$m to about 300 $\mu$m are particularly useful, however, wide variations in thicknesses are permitted and may be desirable for particular constructions. The pore size of the spreading layer can be selected so as to separate components from the blood which might interfere with the optical analysis, e.g., the pore size can be selected to screen out blood cells.

The reagent layer is prepared from a composition including one or more active materials, i.e., materials which interact in the presence of the material to be tested or a by-product thereof, e.g., a precursor or reaction product such as in the case of an element for assaying cholesterol. The particular interactive materials that may be distributed within a reagent layer will depend on the analysis of choice. Materials or compositions that can provide a detectable species which is diffusible such that it can move into a permeable registration layer are preferred. For example, an oxidative enzyme can be incorporated into a reagent layer together with peroxidase or a peroxidative material. Dye-providing compositions can also be used including compositions containing a compound that, when oxidized, couples with itself or with its reduced form to provide a dye. Leuco dyes can also be relied upon to provide the detectable species upon oxidation. Representative compounds which may be distributed in the reagent layer are disclosed in U.S. Pat. No. 4,042,335. The reagent layer construction disclosed in U.S. Pat. No. 4,069,016 for the assay of bilirubin can also be used.

The construction of the support, reagent layer and, in some cases, a second reagent layer, a color-forming layer, a detecting layer, a dye-receiving layer, a radiation-blocking layer, a barrier layer, etc., the process for preparing them, and the method for integrating them to form integrated materials can be conducted according to the descriptions in the aforesaid specifications and in particular U.S. Pat. No. 4,042,335.

The analytical units may be constructed of a registration layer to facilitate the detection of any change produced in the element which relates to detection of the analytical result. The registration layer may be separated from the reagent layer(s) by a radiation-blocking layer, such as a reflecting and/or opaque layer to facilitate the colorimetric detection. Where the detectable species produced in the element is a dye or other mordantable material, the registration layer may contain a mordant, such as described as useful image dye mordants in color photographic films and papers.

A water-permeable radiation-blocking layer comprising a porous metal membrane or a water-permeable radiation-blocking layer containing a metal powder is preferably used in the analytical units as a radiation-blocking layer. Construction, processes for preparing them, and methods for integrating them to form multilayered analytical materials can be practiced according to the descriptions in Japanese Patent Application Nos. 98900/78 and 98902/78 (corresponding to U.S. Patent Application Ser. No. 66,363, filed Aug. 14, 1979, or to West German Patent Application No. P 29 32 973.5, filed Aug. 14, 1979).

Individual analytical units may include a support on the side of the reagent layer opposite to the porous spreading layer. The support can, however, be eliminated and, in such a case, the supporting plate (of the integrated element) also functions as a support for each of the multilayered analytical units.

The liquid sample delivering patch which characterizes this invention may be in the form of a circle, an ellipse, a polygon, a rectangle, a square, and a rhombus. The size (area) thereof is not practically limited but, since a liquid sample reaching the spreading layer is spread to the aforesaid spreading circle at the most, the size of the patch is not necessarily larger than the size of the spreading circle. In order to minimize the amount of a liquid sample applied to the integrated plate, the size of the patch can be determined through experiments. Specifically, it has been found that, when the liquid sample is applied in an amount of 20 $\mu g$ to 60 $\mu g$, a liquid sample-delivering circular patch of 1 cm in diameter is appropriate. From this fact, where the patch is circular, the size is about 3 mm to about 20 mm, preferably about 3 mm to about 10 mm, in radius and, where the patch is of a different shape it should be of a size which can be inscribed within the aforementioned circle. Desirably the patch is about the size of the spreading circle. Of course, with some disposition of the analytical units, it is necessary to use a liquid sample delivering patch having a size greater than that of the spreading circle, and such a case is not outside the scope of the present invention.

The sample delivering patch functions to deliver a liquid sample to the individual analytical units without causing distribution of the chemical composition. In short, it can be analogized to a conduit connecting the applied sample to the individual analytical units and may be likened to a duct or tube. Accordingly, as the sample delivering patch which can be used in the present invention those having a good wettability by the liquid sample and enabling the sample to efficiently diffuse and penetrate therethrough may be used. Unlike the spreading layer, the sample delivering patch is not required to maintain an even distribution of sample throughout the spreading layer. Its function is only to transport sample to the individual analytical units. In this connection, the properties required of the sample delivering patch differ from those of the spreading layer. As the materials for forming the liquid sample delivering patch, there can be used those with a sheet form of about 0.1 mm to about 3 mm in thickness which are made of highly hydrophilic porous materials, such as paper useful for making impregnation paper (e.g., absorbent paper, filter paper, etc.), non-woven fabric, cloth (e.g., gauze, etc.), non-fibrous filtering material (e.g., open-cell type foam sheet, membrane filter with a large pore size, etc.).

Those materials which enable sample solution to spread with a horizontal speed equal to, or more than (preferably several times more than), that of the porous spreading layer used in the analytical units are preferred. In particular, those which also filter most of solid ingredients in the liquid sample are especially preferred. Taking into account the penetrating ability, a suitable pore size of the sample delivering patch is generally about 0.5 $\mu m$ to about 1 mm, preferably about 1 $\mu m$ to about 500 $\mu m$. However, the pore size will depend on the material selected since the material constituting the sample delivering patch may be of various forms as in a membrane filter, e.g., uniformly porous polymer membranes, paper, cloth, etc.

The present invention will now be explained in more detail with reference to the accompanying drawings.

In FIG. 1 liquid sample delivering patch 21 is disposed over a plurality of analytical units 111 and 112 provided in a simple arrangement.

Figure 2:
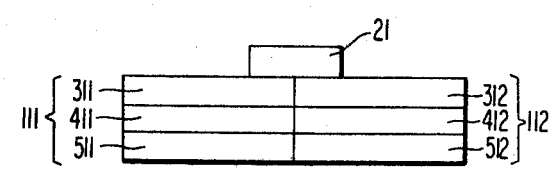

FIG. 2 is a cross-section along the line $X_1$—$Y_1$ of FIG. 1, which shows the different units 111 and 112 comprising porous spreading layers 311 and 312, reagent layers 411 and 412, and transparent supports 511 and 512, respectively, in which a liquid sample delivering patch 21 is provided in contact with the units 111 and 112.

Figure 3:
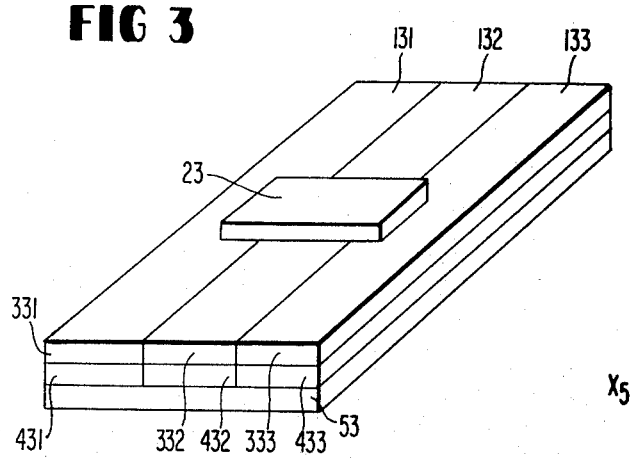
FIGS. 3 and 4 are perspective views of other analytical unit arrangements suitable for use in the invention.

FIG. 3 shows an arrangement wherein three different analytical units are disposed in parallel arrangement, on which a liquid sample delivering patch 23 is disposed. Patch 23 is shown in contact with the porous spreading layers of the units 131, 132, and 133. The three units share a common transparent support 53 having provided thereon respective reagent layers 431, 432, and 433, and porous spreading layers 331, 332, and 333. It is of course also possible to make the porous spreading layers into one common sheet.

Figure 4:
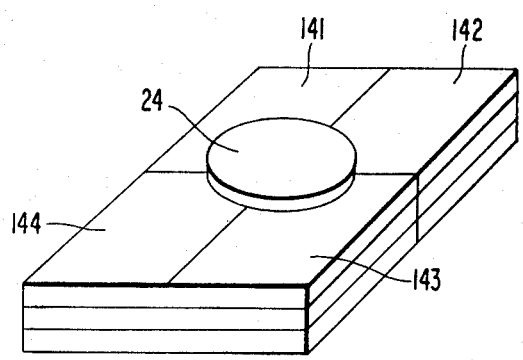

FIG. 4 shows an arrangement wherein four different analytical units 141, 142, 143, and 144 are disposed in a radial pattern with a circular sample delivering patch 24 being located at approximately the radial center. The sample delivering patch 24 may be contacted with the sample spreading layers of the units using an extremely small amount of adhesive, depressing from above using a porous adhesive tape, or by interposing a porous double-coated tape, etc.

Figure 5:
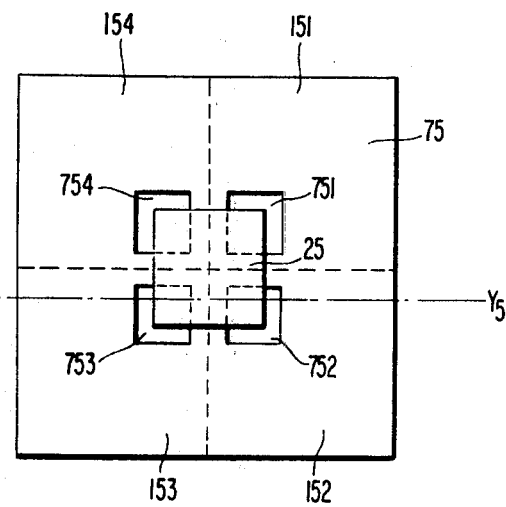
FIGS. 5 and 6 are a specific example of an integrated plate having a waterproof layer with small apertures.
Figure 6:
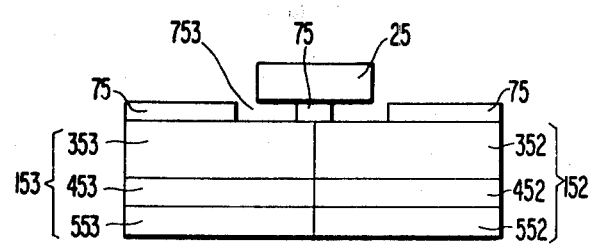

FIGS. 5 and 6 are an example of an integrated plate formed by providing a waterproof layer having one aperture per analytical unit and providing thereover a liquid sample delivering patch. FIG. 5 is an overhead view and FIG. 6 is a vertical cross-sectional view along the line $X_5$—$Y_5$. In this example, waterproof layer 75 having four small apertures 751, 752, 753, and 754 is fixedly mounted on each of the four units 151, 152, 153, and 154, followed by providing liquid sample delivering patch 25. The delivering patch must be directly or indirectly in contact with the porous spreading layers via apertures 751, 752, 753, and 754, though it may not be obvious in these drawings.

While the invention has been described in detail and with reference to specific embodiments thereof, it will be apparent to one skilled in the art that various changes and modifications can be made therein without departing from the spirit and scope thereof.

What is claimed is:

1. An integrated material for chemically analyzing a liquid sample comprising a supporting plate having provided thereon two or more different analytical units each comprising a reagent layer and a porous spreading layer or a portion of a common porous spreading layer, said units being disposed such that at least a portion of the reagent layers are in contact with or in close proximity to one another with said porous spreading layer(s) of said units being commonly covered with a liquid sample delivering patch.

* * * * *